US00PP33560P2

(12) United States Plant Patent
Korlipara

(10) Patent No.: US PP33,560 P2
(45) Date of Patent: Oct. 12, 2021

(54) ***ECHINACEA* PLANTED NAMED 'TNECHSS'**

(50) Latin Name: ***Echinacea* spp.**
Varietal Denomination: TNECHSS

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/212,090

(22) Filed: Mar. 25, 2021

(51) Int. Cl.
*A01H 6/14* (2018.01)
*A01H 5/02* (2018.01)

(52) U.S. Cl.
USPC ..... Plt./428

(58) Field of Classification Search
USPC ..... Plt./428
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'TNECHSS' characterized by a large number of medium inflorescences starting in the first season, very long bloom time with excellent rebloom, a very upright, very compact habit, novel red and green ray florets held horizontally surrounding dark cones, strong upright stems, and excellent vigor.

2 Drawing Sheets

Botanical denomination: *Echinacea* spp.
Variety designation: 'TNECHSS'.
Trademark designation: Sweet Sandia.

BACKGROUND OF THE INVENTION

The present invention relates to a new and distinct cultivar of *Echinacea* and given the cultivar name 'TNECHSS'. *Echinacea* is in the family Asteraceae. The new cultivar is part of a planned breeding program for a container and garden series with compact habits and profuse inflorescences. The exact parents of this selection are unknown, unnamed, proprietary interspecific hybrids bred from *Echinacea paradoxa*, *Echinacea purpurea*, and *Echinacea tennesseensis*.

Compared to *Echinacea* 'TNECHKR' (U.S. Plant Pat. No. 28,768), the new cultivar is shorter and has green and red ray florets.

This new *Echinacea* cultivar is uniquely distinguished by:

1. A very large number of green and red ray florets,
2. very long bloom time with excellent rebloom,
3. very upright, very compact habit,
4. ray florets held horizontally,
5. strong upright stems, and
6. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
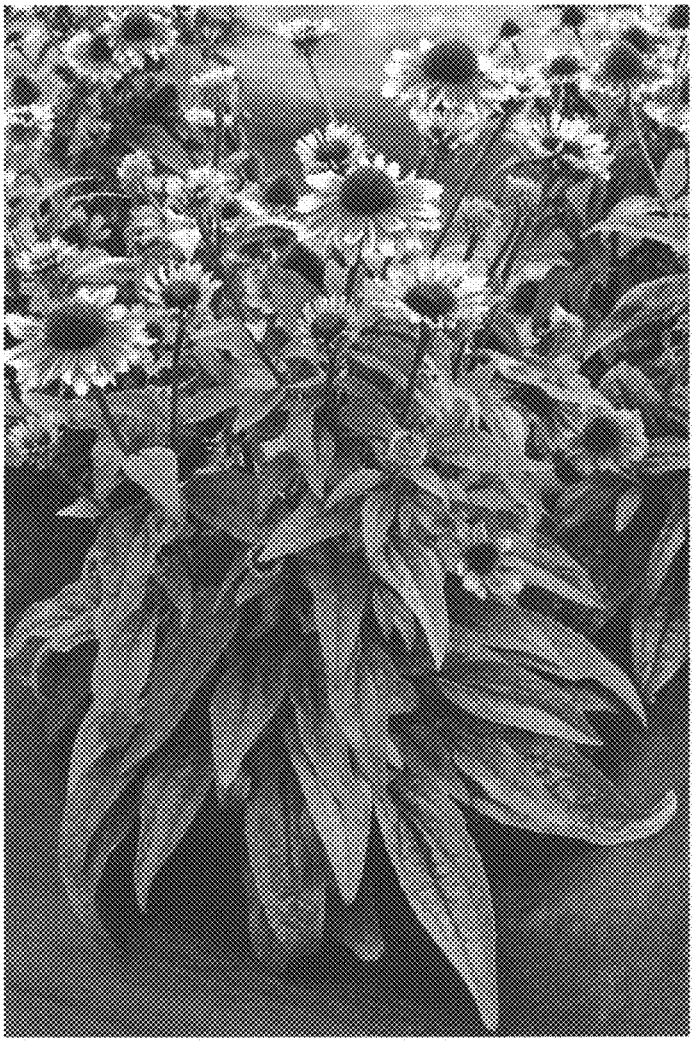
FIG. 1 shows a nine-month-old *Echinacea* 'TNECHSS' growing in the trial field in full sun in late August in Canby, Oreg.
Figure 2:
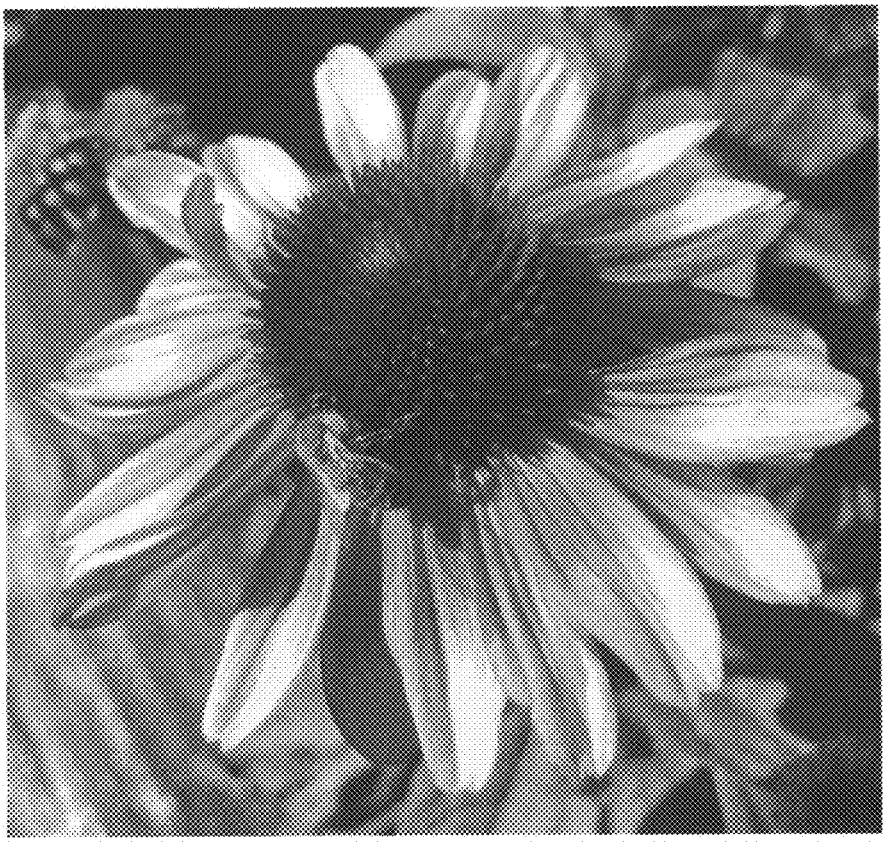
FIG. 2 shows a close up of a nine-month-old *Echinacea* 'TNECHSS' inflorescence.

The following is a detailed description of the new *Echinacea* cultivar based on observations of 9-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type*.—Herbaceous perennial.
*Hardiness*.—USDA Zones 4 to 9.
*Size*.—Grows to 27 cm wide and 40 cm tall to top of inflorescences.
*Form*.—Basal clump, with 9 to 12 stems from the base.
*Vigor*.—Excellent.
*Roots*.—Fibrous, with many downward growing and few laterals, ivory to cream in color, Green White group 157D, roots develop easily from cuttings from the crown.

Leaf (basal):

*Type*.—Simple.
*Shape*.—Lanceolate.
*Arrangement*.—Rosette.
*Blade size*.—Grows to 13.5 cm long and 5.5 cm wide.
*Margins*.—Entire.
*Apex*.—Acuminate.
*Base*.—Attenuate.

*Surface texture*.—Strigose on both sides.
*Venation*.—Pinnate, Yellow Green 147C on both sides.
*Color*.—Topside Green 139A, bottom side closest to Yellow Green N137D.
*Petiole description*.—Clasping, grows to 7 cm long and 5 mm wide, scabrous, narrow leafy edges, which fold downward. Topside Yellow Green 147C in the middle with leaf Green 149A edges, bottom side closest to Yellow Green 147B.

Leaf (stem):
*Type*.—Simple.
*Shape*.—Lanceolate.
*Arrangement*.—Alternate.
*Blade size*.—Grows to 10 cm long and 3.5 cm wide.
*Margins*.—Mostly entire.
*Apex*.—Acuminate.
*Base*.—Attenuate.
*Surface texture*.—Strigose on both sides.
*Venation*.—Pinnate, Yellow Green 147C on both sides.
*Color*.—Topside Green 139A, bottom side closest to Yellow Green N137C.
*Petiole description*.—Clasping, grows to 4 cm long and 3.5 mm wide, scabrous, narrow leafy edges, topside Yellow Green 147B, bottom side Yellow Green 147B.

Inflorescence:
*Type*.—Composite on terminal stalked heads.
*Flowering stem*.—Grows to 40 cm tall from the base of the plant to the terminal inflorescence; unbranched to branched, with 1 to 5 inflorescences per stem; diameter growing to 7 mm wide near the inflorescence; strigose; Yellow Green 147B in shade, tinted N77B in sun.
*Size*.—Grows to 9 cm wide and 3 cm deep as disc enlarges.
*Form*.—Ray florets held horizontally, reflexing somewhat in very old flowers, mature disc is conic.
*Immature inflorescence* (*bud*).—5 cm wide and 1.5 cm deep, ray florets held upright at a 50 degrees angle from vertical, partially contorted and flattening with age Color-144A at apex, changing to Greyed-Red 181A at base, disc color Greyed Orange 187A except the center where N134B.
*Ray florets*.—Without pistil or stamen, about 30 to 33 in number, grow to 33 mm long and 19 mm wide, obovate with the tip two-to-three-toothed (each acute), entire margins, base attenuate, glabrous on both sides; fully open florets topside Greyed Red, 187B at base, Apex Yellow Green 147C, bottom side Greyed Purple 187A; twisting of ray florets, slight.
*Disc*.—Flat becoming conic, becoming 30 mm deep and 40 mm wide with maturity, Greyed Purple 187A in background with bracts Greyed Orange 176A with tips Greyed Purple 187A.
*Disc florets*.—About 400 in number, each with 1 pistil and 4 stamen, grow to 11 mm long and 2 mm wide, each with one persistent, very stiff linear bract (14 mm long with the top 2 mm Greyed Purple 187B to 4 mm Greyed Red 187A to 4 mm Yellow Green 147D to Yellow Green 147A blending to White NN155A on bottom); corolla 7 mm long and 1 mm wide, tubular, 5 lobed, glabrous, Greyed Purple 187B at the base blending to Greyed Purple 187A on lobe tips; pistil 10 mm long, style 5 mm long White NN155A, 2-branched stigma spreading 2 mm wide, Greyed Purple 187A; stamen 4 mm long, filaments 2 mm long and White NN155B, anthers 2.5 mm long and Greyed Brown 199A, pollen slight, Yellow Orange 17B.
*Involucral bracts*.—In 4 to 5 leafy series, area grows to 35 mm wide and 10 mm deep, lobes lanceolate in shape, reflexed, grow to 13 mm long and 3 mm wide, Green N137A, margins strigose, tip acute, strigose on both sides.
*Receptacle*.—Grows to 15 mm wide and 10 mm deep, White NN155B.
*Bloom period*.—June through October in Canby, Oreg.
*Fragrance*.—Faint, floral.
*Lastingness*.—Each inflorescence lasts about four weeks in Canby, Oreg.

Seeds: 3 mm long and 2.5 mm wide, oval, Brown 200C.
*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *